US00PP31329P2

(12) United States Plant Patent
Koppe

(10) Patent No.: US PP31,329 P2
(45) Date of Patent: Jan. 7, 2020

(54) ***BEGONIA* PLANT NAMED 'KRELARE01'**

(50) Latin Name: ***Begonia* x *hiemalis***
Varietal Denomination: KRELARE01

(71) Applicant: Lubbertus H. Koppe, Putten (NL)

(72) Inventor: Lubbertus H. Koppe, Putten (NL)

(73) Assignee: Koppe Royalty B.V., Putten (NL)

( * ) Notice: Subject to any disclaimer, the term of this patent is extended or adjusted under 35 U.S.C. 154(b) by 0 days.

(21) Appl. No.: 16/350,335

(22) Filed: Nov. 2, 2018

(51) Int. Cl.
*A01H 5/02* (2018.01)
*A01H 6/18* (2018.01)

(52) U.S. Cl.
USPC ..... Plt./349

(58) Field of Classification Search
USPC ..... Plt./349
CPC ..... A01H 5/02; A01H 5/0238; A01H 5/00; A01H 6/18; A01H 6/32
See application file for complete search history.

*Primary Examiner* — June Hwu
(74) *Attorney, Agent, or Firm* — C. A. Whealy

(57) ABSTRACT

A new and distinct cultivar of *Begonia* plant named 'KRELARE01' characterized by its compact, upright to outwardly spreading and mounded plant habit; moderately vigorous growth habit; freely branching habit; dark green-colored leaves; freely flowering habit; relatively large double-type flowers that are bright red in color and held above and beyond the foliar plane; and excellent postproduction longevity.

2 Drawing Sheets

Botanical designation: *Begonia* x *hiemalis*.
Cultivar denomination: 'KRELARE01'.

BACKGROUND OF THE INVENTION

The present invention relates to a new and distinct cultivar of *Begonia* plant, botanically known as *Begonia* x *hiemalis*, commercially referred to as an Elatior *Begonia* and hereinafter referred to by the name 'KRELARE01'.

The new *Begonia* plant is a product of a planned breeding program conducted by the Inventor in Ermelo, The Netherlands. The objective of the breeding program is to create new freely-branching *Begonia* plants with excellent postproduction longevity and attractive flower color.

The new *Begonia* plant originated from a cross-pollination made by the Inventor in Ermelo, The Netherlands in January, 2014 of a proprietary selection of *Begonia* x *tuberhybrida* hybrid identified as code number KV10K1753-025, not patented, as the female, or seed, parent with a proprietary selection of *Begonia socotrana* identified as code number S00, not patented, as the male, or pollen, parent. The new *Begonia* plant was discovered and selected by the Inventor as a single flowering plant from within the progeny of the stated cross-pollination in a controlled greenhouse environment in Ermelo, The Netherlands in July, 2014. Asexual reproduction of the new *Begonia* plant by terminal vegetative cuttings taken in a controlled greenhouse environment in Ermelo, The Netherlands since April, 2015 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'KRELARE01'. These characteristics in combination distinguish 'KRELARE01' as a new and distinct *Begonia* plant:

1. Compact, upright to outwardly spreading and mounded plant habit.
2. Moderately vigorous growth habit.
3. Freely branching habit.
4. Dark green-colored leaves.
5. Freely flowering habit.
6. Relatively large double-type flowers that are bright red in color and held above and beyond the foliar plane.
7. Excellent postproduction longevity.

Plants of the new *Begonia* differ primarily from plants of the female parent selection in flower color as plants of the female parent selection have orange-colored flowers. In addition, plants of the new *Begonia* have lighter green-colored leaves than plants of the female parent selection.

Plants of the new *Begonia* differ primarily from plants of the male parent selection in flower color as plants of the male parent selection have pink-colored flowers. In addition, plants of the *Begonia* have double-type flowers whereas plants of the male parent selection have single-type flowers.

Plants of the new *Begonia* can be compared to plants of *Begonia* x *hiemalis* 'Baladin', not patented. In side-by-side comparisons conducted in Ermelo, The Netherlands, plants of the new *Begonia* differ primarily from plants of 'Baladin' in flower color as plants of the new *Begonia* have lighter red-colored flowers than plants of 'Baladin'. In addition, plants of the new *Begonia* are more freely branching than plants of 'Baladin'.

Plants of the new *Begonia* can also be compared to plants of *Begonia* x *hiemalis* 'Veronica', not patented. In side-by-side comparisons conducted in Ermelo, The Netherlands, plants of the new *Begonia* differ primarily from plants of 'Veronica' in the following characteristics:

1. Plants of the new *Begonia* are more compact than and not as upright as plants of 'Veronica'.
2. Plants of the new *Begonia* have larger flowers than plants of 'Veronica'.
3. Plants of the new *Begonia* have double-type flowers whereas plants of 'Veronica' have semi-double-type flowers.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical plant of 'KRELARE01' grown in a container.

The photograph on the second sheet are close up views of the upper (right) and lower (left) surfaces of typical leaves and flowers of 'KRELARE01', and in the center of the photograph is a close-up view of typical flower buds.

DETAILED BOTANICAL DESCRIPTION

The aforementioned photographs and following observations and measurements describe plants grown during the spring and early summer in 12-cm containers in a glass-covered greenhouse in Ermelo, The Netherlands and under cultural practices typical of commercial *Begonia* production. During the production of the plants, day temperatures averaged 20° C. and night temperatures averaged 18° C. Plants were twelve weeks old when the photographs and description were taken. In the following description, color references are made to The Royal Horticultural Society Colour Chart, 2015 Edition, except where general terms of ordinary dictionary significance are used.

Botanical classification: *Begonia* x *hiemalis* 'KRELARE01'.

Parentage:

*Female, or seed, parent*.—Proprietary selection of *Begonia* x *tuberhybrida* hybrid identified as code number KV10K1753-025, not patented.

*Male, or pollen, parent*.—Proprietary selection of *Begonia socotrana* identified as code number S00, not patented.

Propagation:

*Type*.—By terminal vegetative cuttings.

*Time to initiate roots, summer and winter*.—About 20 days at temperatures about 20° C.

*Time to produce a rooted young plant, summer and winter*.—About five weeks at temperatures about 20° C.

*Root description*.—Fine, fibrous; typically white to orange brown in color, actual color of the roots is dependent on substrate composition, water quality, fertilizer type and formulation, substrate temperature and physiological age of roots.

*Rooting habit*.—Freely branching; medium density; plants of the new *Begonia* have not been observed to form tubers.

Plant description:

*Plant habit and form*.—Compact, upright to outwardly spreading and mounded plant habit; overall plant shape, broadly obovate.

*Growth habit*.—Moderately vigorous growth habit and moderate growth rate; suitable for 12-cm and larger containers; under optimal environmental and cultural conditions, usually about nine weeks are required to produce proportional plants in 12-cm containers.

*Branching habit*.—Freely branching with about four primary branches each with about three secondary branches developing per plant.

*Plant height, soil level to top of foliar plane*.—About 19.8 cm.

*Plant height, soil level to top of floral plane*.—About 24.8 cm.

*Plant width*.—About 31.8 cm.

*Lateral branches*.—Length: About 8.3 cm. Diameter: About 9 mm to 11 mm. Internode length: About 1.8 cm. Strength: Moderately strong. Aspect: About 40° from vertical. Texture and luster: Sparsely pubescent; glossy. Color, developing: Close to 144B; at the internodes, close to 146B. Color, developed: Close to 146B; at the internodes, close to 146B. Lenticels: Density: Medium. Length: About 3 mm. Diameter: About 0.5 mm. Shape: Linear. Color: Close to 145B.

*Leaves*.—Arrangement: Alternate, simple. Length: About 11.4 cm. Width: About 9.8 cm. Shape: Broadly ovate, asymmetrical. Apex: Acute. Base: Truncate with cordate tendencies. Margin: Crenate to dentate; moderately and coarsely undulate. Texture and luster, upper surface: Smooth, glabrous; slightly velvety; moderately glossy. Texture and luster, lower surface: Smooth, glabrous; moderately glossy. Venation pattern: Laciniate. Color: Developing leaves, upper surface: Darker than between 147A and N189A. Developing leaves, lower surface: Close to 176A. Fully expanded leaves, upper surface: Darker than 147A; venation, close to 143A. Fully expanded leaves, lower surface: Close to 174A; venation, close to 146B. Petioles: Length: About 5.9 cm. Diameter: About 5 mm. Strength: Low, flexible. Texture and luster, upper and lower surfaces: Sparsely pubescent; moderately glossy. Color, upper surface: Close to N170B; distally, small spot, close to 180A. Color, lower surface: Close to 152B. Stipules: Length: About 1.2 cm. Width: About 1.1 cm. Shape: Broadly ovate to roughly deltoid. Apex: Acute. Base: Broadly cuneate. Margin: Irregularly ciliate. Texture and luster, upper and lower surfaces: Smooth, glabrous; moderately glossy. Color, upper and lower surfaces: Close to 145B; apex and margins, tinged with close to 182B; venation, close to 146C.

Flower description:

*Flower appearance and flowering habit*.—Double-type rotate flowers with four tepals and numerous tepaloids; flowers arranged in axillary compound cymes; freely flowering habit with typically about nine flowers per cyme and about 540 flowers and flower buds developing per plant; many cymes in flower simultaneously; flowers positioned above and beyond the foliar plane and face upright to outwardly; only male flower development has been observed to date on plants of the new *Begonia*.

*Natural flowering season*.—Plants begin flowering about five weeks after planting; plants will flower year round regardless of nyctoperiod, however plants flower earlier and more abundantly from spring into the autumn in The Netherlands.

*Postproduction longevity*.—Individual flowers last about ten days on the plant; flowers not persistent; excellent postproduction longevity, plants maintain good substance for about 50 days in an interior environment.

*Fragrance*.—None detected.

*Inflorescence height*.—About 9.4 cm.

*Inflorescence diameter*.—About 11.3 cm.

*Flowers*.—Shape: Rotate, double-type. Diameter: About 6.5 cm by 6.5 cm. Depth (height): About 2.7 cm.

*Flower buds*.—Length: About 1.6 cm. Diameter: About 0.6 cm to 1.5 cm. Shape: Broadly ovate to nearly circular, flattened. Texture and luster: Glabrous; slightly velvety; slightly glossy. Color: Close to 42A to 42C.

*Tepals*.—Quantity and arrangement per flower: Usually about four per flower arranged in two whorls. Length, lower tepals: About 3.8 cm. Width, lower tepals: About 3.8 cm. Length, upper tepals: About 2.9 cm. Width, upper tepals: About 2.9 cm. Shape, all tepals: Broadly obovate to nearly orbicular. Apex, all tepals: Rounded. Base, all tepals: Reniform. Margin, lower tepals: Entire; not undulate. Margin, upper tepals: Crenate; not undulate. Texture and luster, upper and lower surfaces, all tepals: Smooth, glabrous; moderately velvety; matte. Color, lower tepals: When opening, upper surface: Close to 44B; towards the margins and apex, close to 44A. When opening, lower surface: Close to 44C to 44D; towards the margins and apex, close to 42B. Fully opened, upper surface: Close to 44B; towards the margins and apex, close to 44A; venation, similar to lamina color; color does not change with development. Fully opened, lower surface: Close to 48A, 48B and 49C; venation, close to 34D; color does not change with development. Color, upper tepals: When opening, upper surface: Close to 44B; towards the margins and apex, close to 44A. When opening, lower surface: Close to 45C. Fully opened, upper surface: Close to 44B; towards the margins and apex, close to 44A; venation, similar to lamina color; color does not change with development. Fully opened, lower surface: Close to 43C; towards the margins and apex, close to 43B; venation, close to 34D; color does not change with development.

*Tepaloids*.—Quantity and arrangement per flower: Typically about 9 to 13 per flower clustered at the center of the flower. Length: About 2.4 cm to 2.8 cm. Width: About 1.8 cm to 2.7 cm. Shape: Obovate. Apex: Obtuse to broadly and shallowly emarginate. Base: Attenuate. Margin: Entire to irregularly crenate; slightly undulate. Texture and luster, upper and lower surfaces: Smooth, glabrous; moderately velvety; matte. Color: When opening, upper surface: Close to 44B; towards the margins and apex, close to 44A. When opening, lower surface: Close to 45C; towards the margins, close to 44B. Fully opened, upper surface: Close to 43A; venation, similar to lamina color; color does not change with development. Fully opened, lower surface: Close to 43B; venation, similar to lamina color; color does not change with development.

*Peduncles*.—Length: About 7.6 cm. Diameter: About 5 mm to 6 mm. Strength: Moderately strong. Aspect: About 25° from lateral branch axis. Texture and luster: Smooth, glabrous; moderately glossy. Color: Close to 146C.

*Pedicels*.—Length: About 2.3 cm. Diameter: About 2 mm. Strength: Moderately strong. Aspect: About 20° from peduncle axis. Texture and luster: Smooth, glabrous; glossy. Color: Close to N170B.

*Flower bracts*.—Quantity per flower: Two. Length: About 1.7 cm. Width: About 1.5 cm. Shape: Broadly ovate. Apex: Acute. Base: Broadly cuneate. Margin: Finely ciliate. Texture and luster, upper and lower surfaces: Smooth, glabrous; slightly glossy. Color, upper and lower surfaces: Close to 146D; margins and apex tinged with close to 179B; venation, close to 146A.

*Reproductive organs*.—Stamens transformed into tepaloids; flowers are sterile. Female flower development has not been observed on plants of the new *Begonia* to date; no seed nor fruit production has been observed to date.

Disease & pest resistance: Resistance to pathogens and pests common to *Begonia* plants has not been observed on plants of the new *Begonia* to date.

Temperature tolerance: Plants of the new *Begonia* have been observed to tolerate high temperatures of about 35° C. and to be suitable for USDA Hardiness Zones 10 to 12.

It is claimed:

1. A new and distinct *Begonia* plant named 'KRELARE01' as illustrated and described.

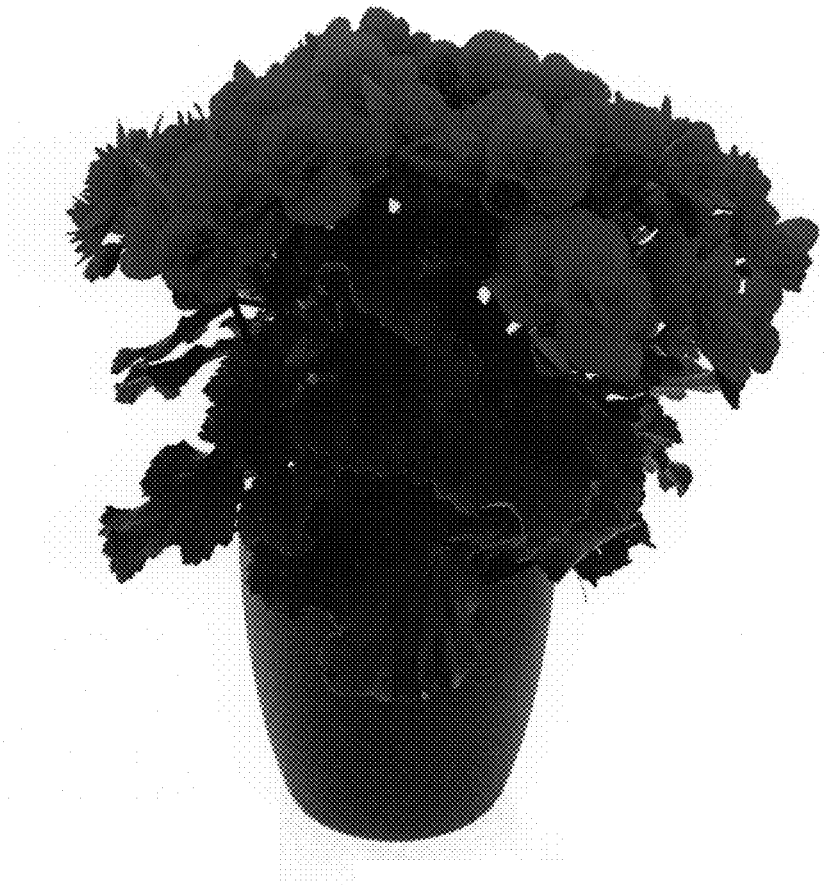

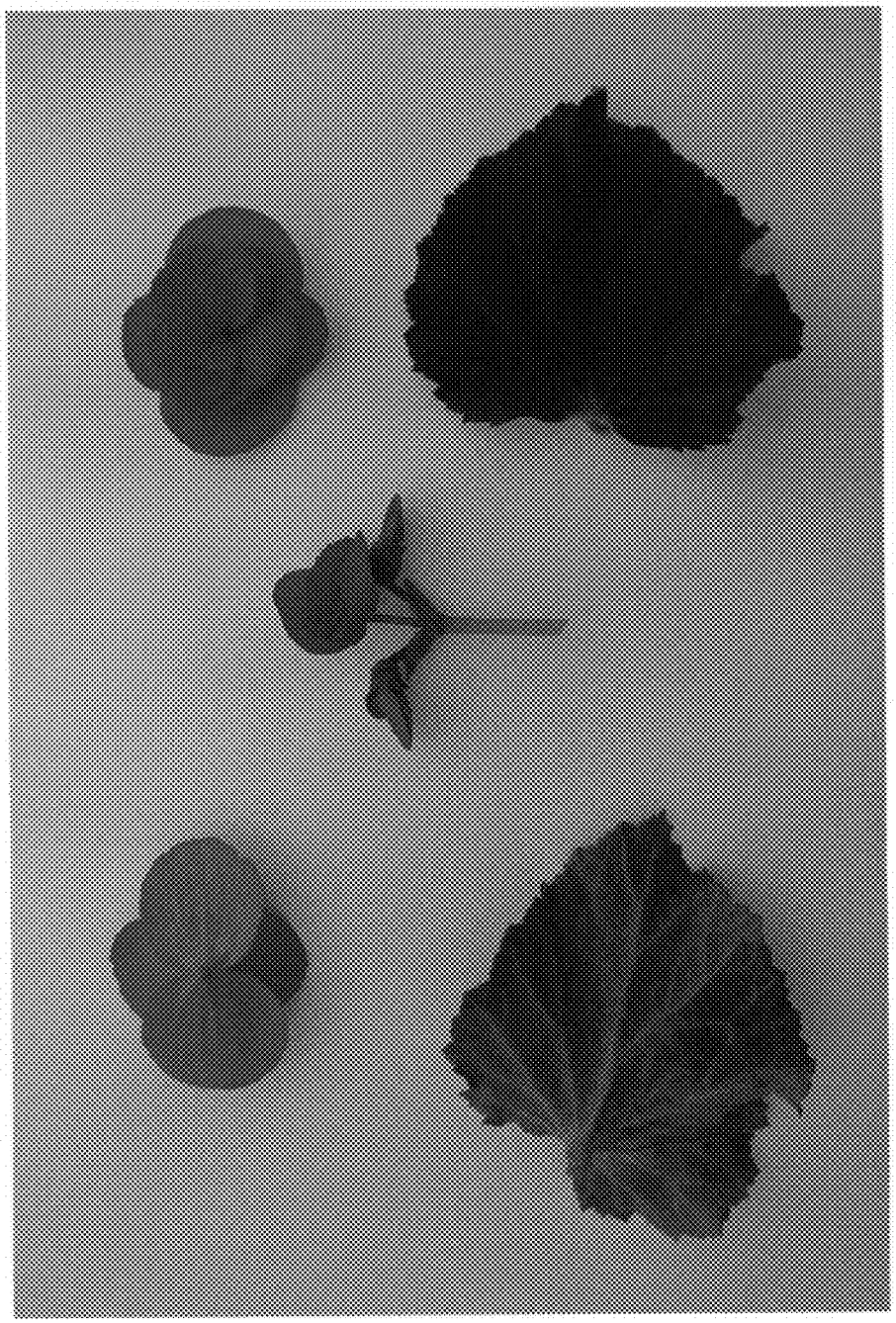

* * * * *